United States Patent [19]

Raines

[11] Patent Number: 5,366,312
[45] Date of Patent: Nov. 22, 1994

[54] SURGICAL SAW BLADE ATTACHMENT ASSEMBLY

[75] Inventor: Aaron T. Raines, Dallas, Tex.
[73] Assignee: Surgiquip, Inc., Dallas, Tex.
[21] Appl. No.: 108,340
[22] Filed: Aug. 18, 1993
[51] Int. Cl.5 .......................... F16B 7/00; B24B 41/04
[52] U.S. Cl. .......................................... 403/3; 403/13; 403/260; 30/340; 83/698.11
[58] Field of Search ................. 403/3, 4, 337, 13, 261, 403/260, 259; 30/275.4, 277.4, 340; 83/698.41, 698.11, 666

[56] References Cited

U.S. PATENT DOCUMENTS

| | | | |
|---|---|---|---|
| 2,296,058 | 9/1942 | Rubinstein | 403/3 |
| 2,497,217 | 2/1950 | Hall | 403/3 |
| 4,343,214 | 8/1982 | Schadlich | 83/698.41 X |
| 4,558,614 | 12/1985 | Harris | 83/56 |
| 4,729,193 | 3/1988 | Gant et al. | 83/666 X |
| 4,850,109 | 7/1989 | Kerwin | 403/3 X |
| 5,251,524 | 10/1993 | Clifford | 83/383 |

Primary Examiner—John T. Kwon
Assistant Examiner—Hoang Nguyen
Attorney, Agent, or Firm—Ross, Howison, Clapp & Korn

[57] ABSTRACT

A universal attachment assembly for securing saw blades of different mounting configuration to the actuator shaft of an oscillating surgical saw. The blade is held firmly between a fixed receptor plate on the shaft and the selected surface of a selected profiled mounting disk by a locking nut. Each side of each mounting disk is differently profiled to mate with a different saw blade.

5 Claims, 3 Drawing Sheets

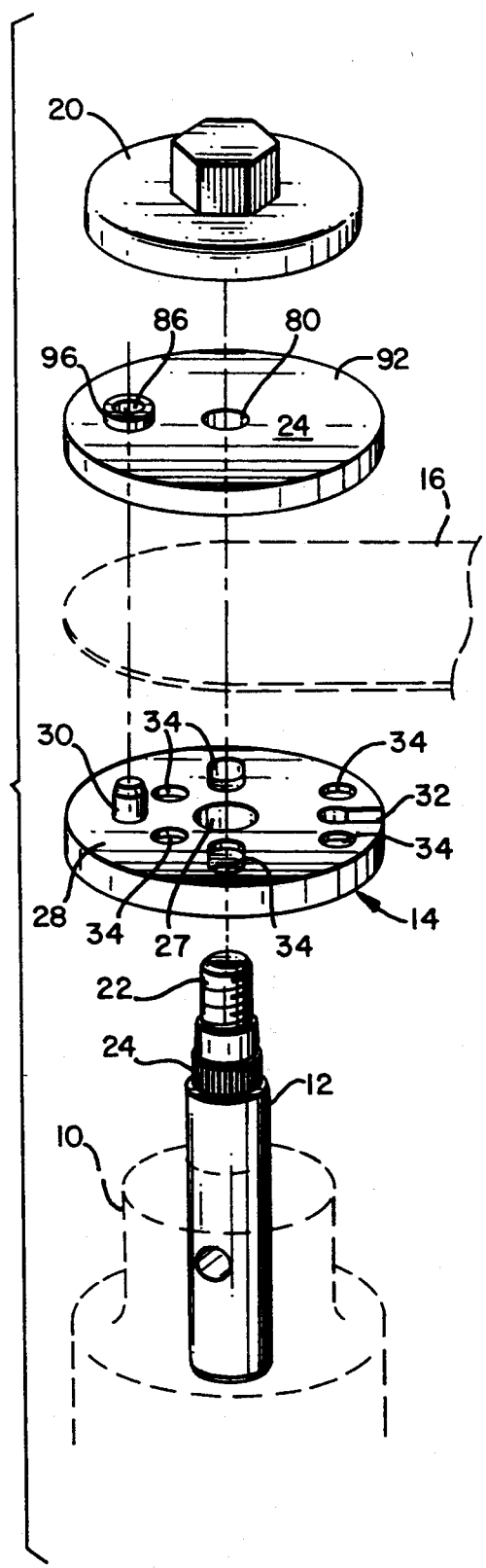
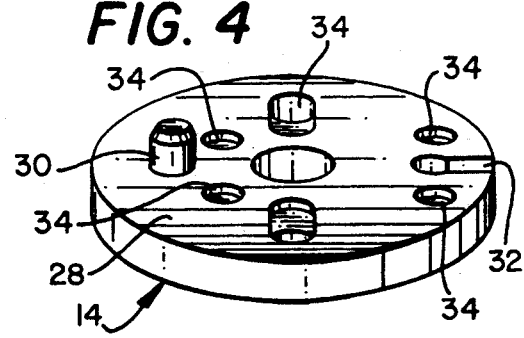
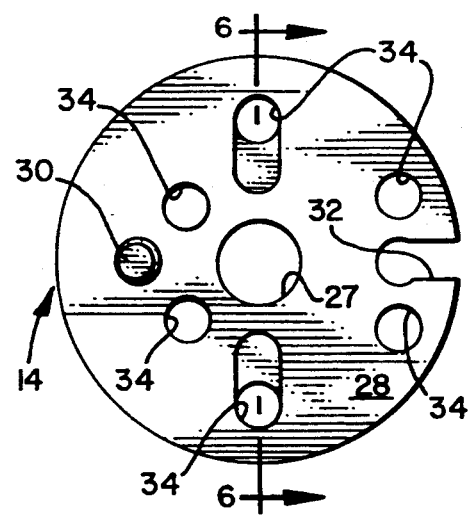
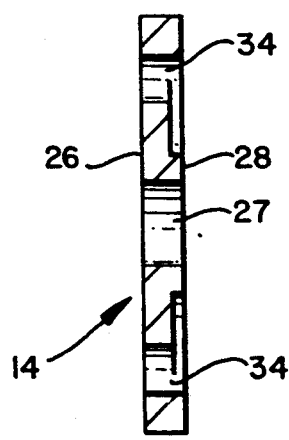

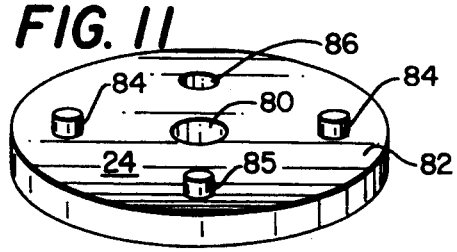
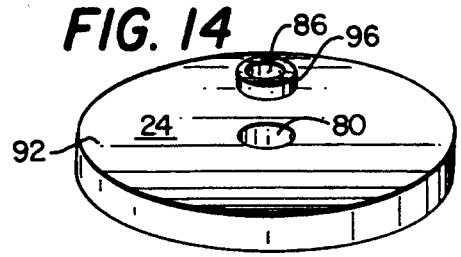
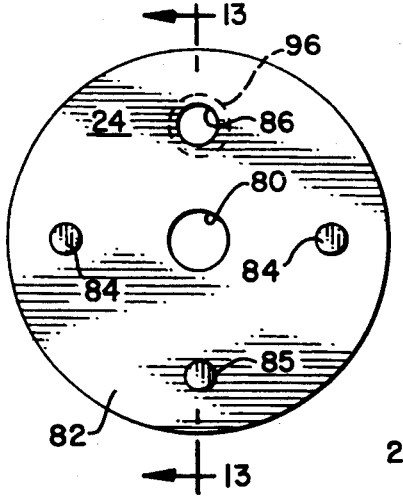
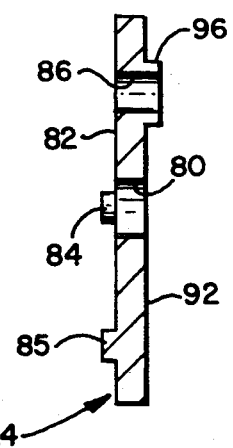
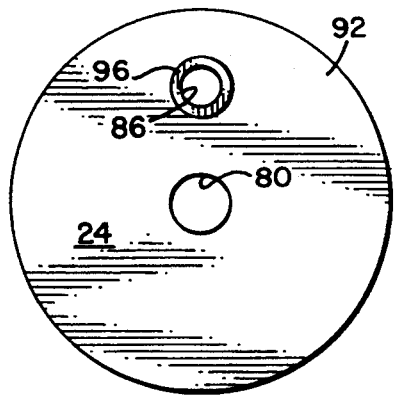
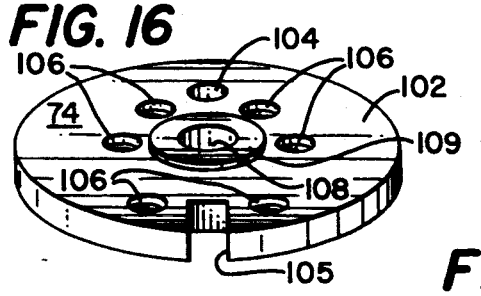
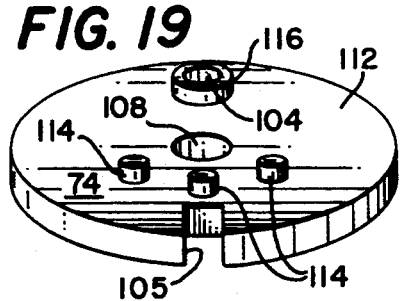
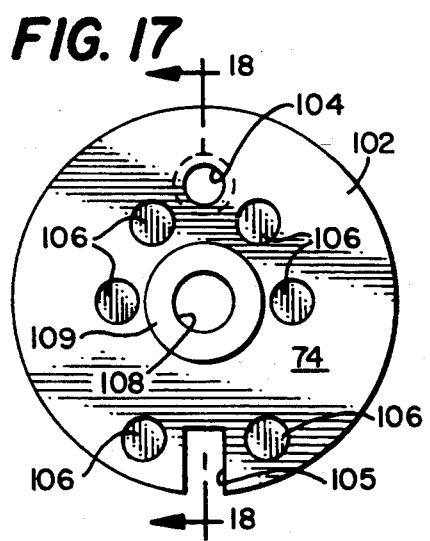
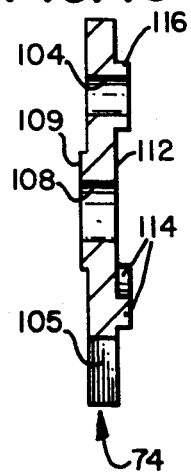
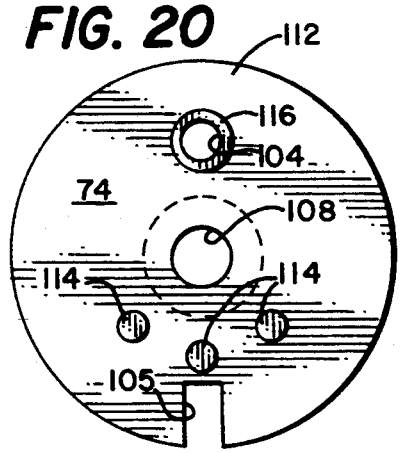

SURGICAL SAW BLADE ATTACHMENT ASSEMBLY

TECHNICAL FIELD OF THE INVENTION

This invention relates to oscillating surgical saws, and more particularly, to a surgical saw blade attachment assembly adaptable to securement of a plurality of different surgical saw blades in operative position on an oscillating saw.

BACKGROUND OF THE INVENTION

Oscillating saws for cutting bone during surgical procedures have been widely used. Such saws typically employ a replaceable saw blade securely mounted on a shaft which rapidly oscillates back and forth through an angle of about 5° to 7°. The rapidity and constancy of the reversal of direction of the actuating shaft necessitates an interconnection between the shaft and blade that is substantially free of mutual vibration. The requirements placed upon the surgical saw blade have caused surgical saw manufacturers to provide special configurations at the proximal end of their blades in order to mate closely with receiving structure associated with the actuating shaft of the saw.

This invention is directed to an attachment assembly for saw blades which is readily adaptable to securing the saw blades of different manufacturers, having different attachment configurations, in a fixed relationship to the actuating shaft.

SUMMARY OF THE INVENTION

In accordance with the invention, there is provided an attachment mechanism for securing a plurality of different saw blades, 2 having different mounting configurations, to the actuating shaft of an oscillating saw. The mechanism includes a receptor plate mounted in fixed position on the saw actuator shaft to receive the proximal end of a saw blade. A mounting disk is mountable on the shaft over the positioned saw blade to mate with the blade and receptor plate, and this mounting disk is profiled differently on each of its two sides. Each side of the disk is profiled to mate with at least one saw blade configuration. Locking means is mounted at the end of the shaft to press the disk, blade and receptor plate together in fixed operating position with respect to the shaft.

In a particular embodiment of the invention, a plurality of mounting disks are provided, each face of which has a different profile adapted to match with different surface configurations on the upper side of the proximal end of a saw blade. In each instance, the mounting disk has an aperture for receiving a mounting post carried by the receptor plate.

Utilization of the invention permits rapid and secure mounting of blades of different configuration to the saw. Simply by selecting the appropriate mounting disk and positioning the disk surface which corresponds to the particular saw blade configuration selected, the user may securely mount any selected blade to the saw for operation.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 3 is an exploded view showing the assembly of the components of FIG. 2;

FIG. 4 is a perspective view of the receptor plate for permanent mounting on the saw actuator shaft in the assembly of FIGS. 1–3;

FIG. 5 is a plan view of the receptor plate shown in FIG. 4;

FIG. 6 is a cross-sectional view taken along the line 6—6 in FIG. 5;

FIG. 11 is a perspective view illustrating the mounting profile of one side of a first mounting disk constructed in accordance with the invention which side is operatively employed with the blade of FIG. 7 as shown in FIGS. 1–3;

FIG. 12 is a plan view of the mounting disk shown in FIG. 11;

FIG. 13 is a cross-sectional view of the first mounting disk illustrated by FIGS. 11–12, taken along the line 12–13 appearing in FIG. 12;

FIG. 14 is a perspective view illustrating the profile of the opposite side of the mounting disk illustrated in FIG. 11;

FIG. 15 is a plan view of the side of the first mounting disk illustrated in FIG. 14;

FIG. 16 is a perspective view illustrating the profile of one side of a second mounting disk constructed in accordance with the invention;

FIG. 17 is a plan view of the second mounting disk as illustrated by FIG. 16;

FIG. 18 is a cross-sectional view illustrating the second mounting disk shown in FIGS. 16–17, taken along line 18—18 shown in FIG. 17;

FIG. 19 is a perspective view illustrating the mounting configuration of the opposite side of the second mounting disk illustrated in FIG. 16; and FIG. 20 is a plan view showing the side of the second mounting disk as illustrated in FIG. 19.

DESCRIPTION OF THE PREFERRED EMBODIMENTS

Figure 1:
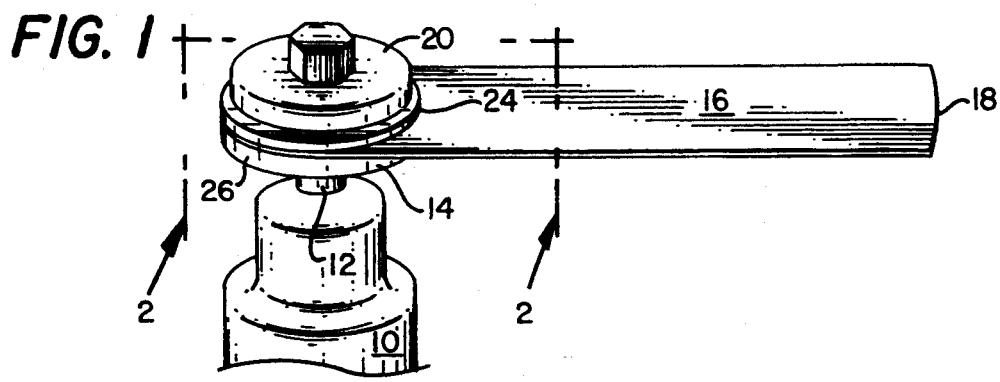
FIG. 1 is a perspective view showing a saw blade secured to an actuating shaft of a surgical saw by an attachment assembly constructed in accordance with the present invention.

In accordance with the invention, as seen in FIG. 1, a surgical saw 10 is provided with an oscillating actuator shaft 12 extending therefrom. As is conventional in oscillating surgical saws, actuator shaft 12 is rapidly oscillated by saw 10 through a small acute angle of rotation, usually about 5° to 7°. The attachment mechanism of this invention includes a universal receptor plate 14 mounted on shaft 12 for oscillation therewith. A saw blade 16 having cutting edge 18 at its distal end is mounted for oscillation with actuator shaft 12 atop universal receptor plate 14. A locking nut 20 secures the assembly together by being threaded down tightly upon threaded end 22 of actuator shaft 12, as seen in FIG. 1. A mounting disk 24 directly engages the top surface of saw blade 16, so that together the receptor plate 14, saw blade 16, mounting disk 24 and locking nut 20 form a unit pressed together for fixed oscillation with shaft 12.

Figure 2:
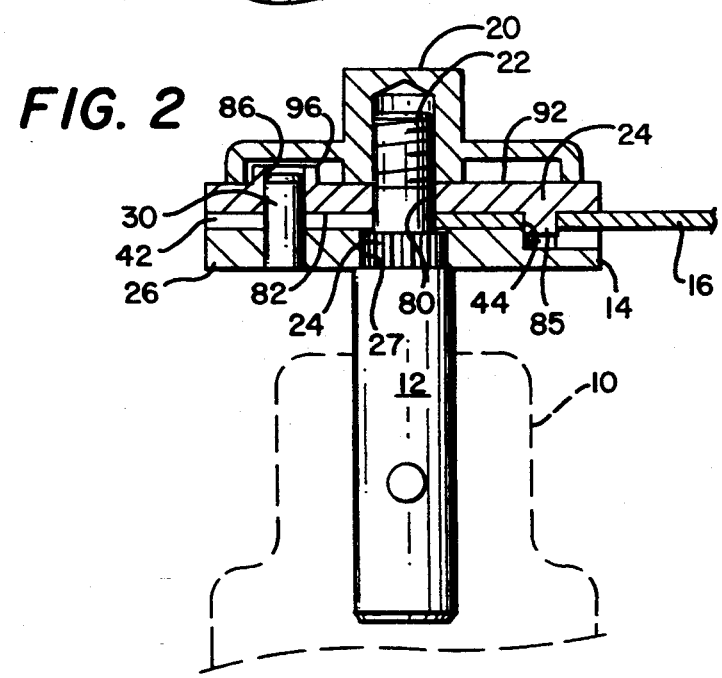
FIG. 2 is a cross-section of the device illustrated in FIG. 1, depicting a particular blade and mounting disk deployed.

As seen in FIG. 2, receptor plate 14 is secured to shaft 12 by a press fit on knurled section 24 of shaft 12. Other methods for permanent securement of receptor plate 14 on shaft 12 may be utilized. Universal receptor plate 14 is illustrated in more detail in FIGS. 4 through 6. Receptor plate 14 has a flat bottom surface 26 which faces toward the saw when mounted on shaft 12. A central aperture 27 extends through receptor plate 14 for snugly receiving shaft 12 therethrough. Upper surface 28 of receptor plate 14 includes a mounting post 30 extending upwardly therefrom spaced from central aperture 27. Diametrically opposed from mounting post 30 on surface 28 is a relief slot 32 extending inwardly from an edge of receptor plate 14. Six apertures 34 are spaced about receptor plate 14. The profile of surface 28 on receptor plate 14 is adapted to receiving each of a plurality of different saw blade configurations flat against surface 28.

Four saw blade mounting configurations which may be mounted in the universal attachment mechanism are depicted in FIGS. 7–10. Each of the Figures represents a family of blades. The different blades in each family have different working ends, but share the same proximal mounting profile illustrated in the drawings. Blade 16 shown in FIG. 7 includes a proximal circular attachment section 40 having a mounting slot 42 adapted to being positioned on actuator shaft 12. An array of nine spaced apertures 44 are circumferentially arranged on circular portion 40.

Figure 8:
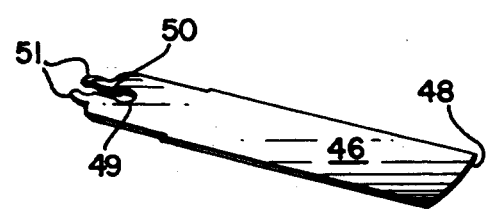
FIG. 8 illustrates a second configuration of saw blade with which the mechanism of this invention may be employed.

A second saw blade 46 which may be secured by the universal attachment apparatus of this invention is depicted in FIG. 8, and has a distal cutting edge 48. Mounting aperture 49 is provided on blade 46 for receiving actuator shaft 12. A slot 50 extends from mounting aperture 49, between spaced confronting mounting arms 51, to the proximal end of blade 46.

Figure 9:
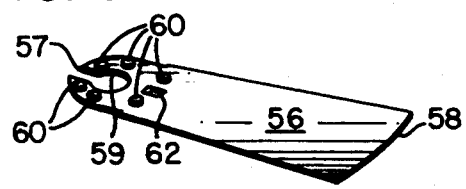
FIG. 9 illustrates a third configuration of saw blade with which the mechanism of this invention may be employed.

A third blade 56 with which the universal attachment mechanism may be used is depicted in FIG. 9. The blade 56 has a distal cutting edge 58. Blade 56 has, at its proximal end, a slot 57 leading to mounting aperture 59 for fitting on actuator shaft 12. Six raised bosses 60 are positioned on one surface of blade 56. A downwardly extending detent 62 is formed distally of aperture 59, and represents the only downwardly extending profiling of any of the saw blades illustrated in FIGS. 7 through 10.

Figure 10:
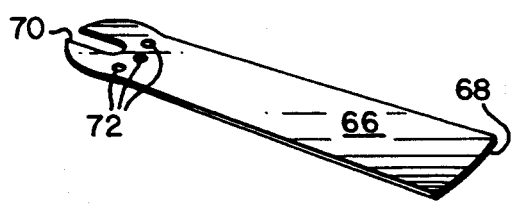
FIG. 10 illustrates a fourth configuration of saw blade with which the mechanism of this invention may be employed.

Blade 66, depicted in FIG. 10, has a distal cutting edge 68, and a mounting slot 70 located at its proximal edge. Three spaced mounting apertures 72 extend through blade 66 at spaced locations distal to slot 70.

It will be appreciated that all of the saw blades in FIGS. 7 through 10 may be placed flat against upper surface 28 of universal receptor plate 14. Relief slot 32 in plate 14 may receive detent 62 of blade 56.

In order to secure each of the blades 16, 46, 56 and 66 in operating position, two mounting disks 24 and 74, used in the alternative, are provided. Disk 24 is depicted in detail in FIGS. 11 through 15, while mounting disk 74 is illustrated by FIGS. 16 through 20. Each of the mounting disks 24 and 74 have a differently profiled surface on their opposite faces, so that each of the four surfaces of mounting disks 24 and 74 are adapted to retain a different one of the prior art saw blades illustrated in FIGS. 7 through 10.

Mounting disk 24 has a central aperture 80 for receiving actuator shaft 12. An aperture 86 extends through disk 24, outward from aperture 80 a distance corresponding to the spacing between the central aperture 27 of receptor plate 14 and the mounting post 30. A circular mounting boss 85 diametrically opposed to aperture 86 extends upwardly from surface 82 of disk 24. Circular mounting bosses 84 extending from surface 82 are diametrically opposed along a diameter perpendicular to the diameter extending between aperture 86 and boss 85. The profiling of surface 92 also includes an annular boss 96 which surrounds aperture 86.

Figure 7:
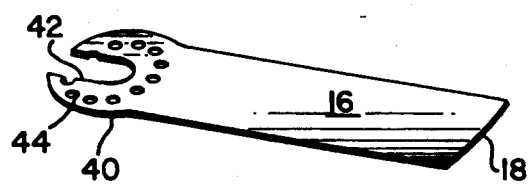
FIG. 7 shows one configuration of saw blade with which the mechanism of this invention may be employed.

FIGS. 2 and 3 depict the use of mounting disk 24, and more particularly surface 82 thereof, to secure blade 16 illustrated in FIG. 7 in operating position on saw 10. Boss 85 extends through the aperture 44 which is positioned on the center line of blade 16. Bosses 84 mate with the apertures 44 of blade 16 which are spaced along a line extending at right angles to the center line of blade 16. Mounting post 30 of receptor plate 14 extends upwardly through slot 42 of blade 16 and into aperture 86 of the mounting disk 24. The mounting disk 24, blade 16 and receptor plate 14 are thus secured together when nut 20 is tightened on threaded shaft end 22.

The surface 92 of mounting disk 24 may be utilized to mount blade 46 illustrated in FIG. 8. When it is desired to replace the blade 16 illustrated in FIGS. 2 and 3, with blade 46, the locking nut 20 and mounting disk 24 are removed, and blade 16 replaced by blade 46. Then mounting disk 24 is replaced with surface 92 confronting blade 46. Annular boss 96 is engaged by arms 51 of blade 46 when the mounting disk 24 is placed on actuator shaft 12.

The second mounting disk 74, shown in FIGS. 16–20, may be alternatively utilized to mount either of blades 56 or 66. Mounting disk 74 includes aperture 104 for receiving mounting post 30 of receptor plate 14. Slot 105 extends into the periphery of disk 74 opposite aperture 104. Disk 74 also includes six spaced circular depressions on surface 102, corresponding in spacing to the raised bosses 60 of blade 56. Mounting disk 74 is provided with central aperture 108 for receiving actuator shaft 12. Surface 102 is provided with a raised annular boss 109 surrounding central aperture 108. The opposite surface of mounting disk 74, indicated by reference numeral 112, includes three spaced circular bosses corresponding to the three apertures 72 of blade 66. On surface 112, aperture 104 is surrounded by a round boss 116, corresponding in width to the slot 70 on blade 66.

Surface 102 of mounting disk 74 is utilized by placing it downwardly over blade 56 so that boss 109 is received in aperture 59 of blade 56. Circular depressions 106 on disk 74 receive the raised bosses 60 of blade 56. If the use happens to place blade 56 so that the bosses 60 shown in FIG. 9 are facing downwardly toward receptor plate 14, the bosses will be received in apertures 34.

In order to mount blade 66, surface 112 is placed downwardly on blade 66. Bosses 114 are received in apertures 72 of blade 66, and boss 116 fits snugly between the sides of slot 70 on blade 66.

It will be appreciated that with the simple provision of two mounting disks, provision is made for quickly and easily attaching any blade having one of four different mounting configurations to saw 10. The appropriate mounting disk for the blade selected is utilized with its mating surface facing downwardly toward the blade. The securement of the blade in operating relationship is quickly effected by tightening of nut 20 to complete the mounting. Of course, additional blade configurations may be accommodated by the provision of additional profiled mounting disks.

Whereas the present invention has been described with respect to specific embodiments thereof, it will be understood that various changes and modifications will be suggested to one skilled in the art and it is intended to encompass such changes and modifications as fall within the scope of the appended claims.

I claim:

1. An attachment mechanism for securing a plurality of different blades having different mounting configurations formed on the ends thereof to an oscillating saw employing an oscillating actuator shaft comprising:
   a receptor plate mounted in fixed position on the shaft for receiving one end of a saw blade;
   a first mounting disk mountable on the shaft, each side of the disk being profiled to mate with a different one of the configurations of such saw blades; and
   locking means mountable over the end of the shaft to press the disk, blade and receptor plate together in fixed operating position with respect to the shaft.

2. The mechanism of claim 1, wherein the receptor plate carries a mounting post, and the mounting disk includes an aperture for receiving the mounting post.

3. The mechanism of claim 1, wherein said shaft is threaded, and the locking means is a threaded nut mating with the shaft.

4. The mechanism of claim 3, wherein the threaded nut has a diameter smaller than the diameter of the first mounting disk.

5. An oscillating saw blade attachment kit for securing a plurality of different blades having different mounting configurations formed on the ends thereof to an oscillating saw employing an oscillating actuator shaft comprising:
   a receptor plate mounted in fixed position on the shaft for receiving one end of a saw blade;
   a first mounting disc mountable on the shaft, each side of the disc being profiled to mate with a different one of the configurations of such saw blade;
   a second mounting disc adapted for use in the alternative to said first mounting disc, each side of said second mounting disc being profiled to mate with an additional saw blade configuration; and
   locking means mountable over the end of the shaft to press one of the mounting discs, blade and receptor plate together in fixed operating position with respect to the shaft.

* * * * *